United States Patent
Kappel et al.

(10) Patent No.: US 6,870,650 B2
(45) Date of Patent: Mar. 22, 2005

(54) ILLUMINATION DEVICE AND METHOD FOR LASER PROJECTOR

(75) Inventors: David Kappel, San Diego, CA (US); Robert E. Fischer, Westlake Village, CA (US); Biljana Tadic-Galeb, Thousand Oaks, CA (US)

(73) Assignee: Riake Corporation, Houston, TX (US)

( * ) Notice: Subject to any disclaimer, the term of this patent is extended or adjusted under 35 U.S.C. 154(b) by 0 days.

(21) Appl. No.: 10/453,960

(22) Filed: Jun. 4, 2003

(65) Prior Publication Data

US 2004/0008392 A1 Jan. 15, 2004

Related U.S. Application Data

(63) Continuation of application No. 09/682,178, filed on Jul. 31, 2001, now Pat. No. 6,606,173.
(60) Provisional application No. 60/257,061, filed on Dec. 20, 2000, provisional application No. 60/257,047, filed on Dec. 20, 2000, provisional application No. 60/257,062, filed on Dec. 20, 2000, provisional application No. 60/257,063, filed on Dec. 20, 2000, provisional application No. 60/257,045, filed on Dec. 20, 2000, provisional application No. 60/257,046, filed on Dec. 20, 2000, provisional application No. 60/284,455, filed on Apr. 18, 2001, provisional application No. 60/282,738, filed on Apr. 10, 2001, provisional application No. 60/282,376, filed on Apr. 9, 2001, provisional application No. 60/282,735, filed on Apr. 10, 2001, provisional application No. 60/282,737, filed on Apr. 10, 2001, provisional application No. 60/282,734, filed on Apr. 10, 2001, and provisional application No. 60/222,301, filed on Aug. 1, 2000.

(51) Int. Cl.[7] .................................................. G02B 5/32
(52) U.S. Cl. ............................. 359/15; 359/20; 359/599
(58) Field of Search ............................... 359/13, 15, 20, 359/599; 362/558; 353/102, 202

(56) References Cited

U.S. PATENT DOCUMENTS

| | | | | |
|---|---|---|---|---|
| 5,757,544 A | * | 5/1998 | Tabata et al. | 359/434 |
| 6,369,779 B1 | * | 4/2002 | Bartlett | 345/8 |
| 6,606,173 B2 | * | 8/2003 | Kappel et al. | 359/15 |
| 6,714,328 B2 | * | 3/2004 | Steiner | 359/15 |

* cited by examiner

*Primary Examiner*—Leo Boutsikaris
(74) *Attorney, Agent, or Firm*—Law Offices of Mark L. Berrier

(57) ABSTRACT

Systems and methods for providing illumination suitable for imaging devices such as laser projection systems. In one embodiment, a highly collimated (e.g., laser light) beam is passed through a holographic diffuser to create a well defined cone angle for the light emanating from each point on the diffuser. This light is focused into an illumination image that is controlled by the prescription of the diffuser. In one embodiment, the image is a uniformly intense rectangle having a 4:3 aspect ratio to match an imager for a projection display. The diffuser prescription and resulting illumination image can be selected to match any desired imager. The present systems and methods may provide the advantages of high level of light efficiency, reduction or elimination of speckle and "worminess" and reduction or elimination of $\cos ine^4$ and gaussian intensity falloff, all of which are common in prior art designs.

19 Claims, 9 Drawing Sheets

ILLUMINATION DEVICE AND METHOD FOR LASER PROJECTOR

RELATED APPLICATIONS

This application is a continuation of and claims the benefit of and hereby incorporates by reference U.S. patent application Ser. No. 09/682,178, filed on Jul. 31, 2001 now U.S. Pat. No. 6,606,173, entitled "Illumination Device and Method for Laser Projector", which claims the benefit of the following U.S. provisional applications under 35 U.S.C. 119(e) which are all hereby incorporated by reference as if fully set forth herein: Ser. No. 60/222,301, filed on Aug. 1, 2000 entitled "Method and Apparatus for Combining Parallel Collimated Lightbeams", Ser. No. 60/257,061, filed on Dec. 20, 2000 entitled "Method and Apparatus for Combining Parallel Collimated Lightbeams", Ser. No. 60/257,047, filed on Dec. 20, 2000 entitled "Method and Apparatus for Combining Parallel Collimated Lightbeams", Ser. No. 60/257,062 filed on Dec. 20, 2000 entitled "Method and Apparatus for Eliminating Zero-Order Light Leak in an Illumination Device", Ser. No. 60/257,063, filed on Dec. 20, 2000 entitled "Method and Apparatus for Providing an Illumination Source Using a Segmented Diffuser"; Ser. No. 60/257,045, filed on Dec. 20, 2000 entitled "Method and Apparatus for Combining Polychromatic Light Beams Using an Achromatic Diffuser, Ser. No. 60/257,046, filed on Dec. 20, 2000 entitled "Illumination Device Using Multiple Laser Light Sources and Having a Zero-Order Light Leak Correction, Ser. No. 60/284,455, filed on Apr. 18, 2001 entitled "Method and Apparatus for Providing Selectable Illumination Sources", Ser. No. 60/282,738, filed on Apr. 10, 2001 entitled "Polychromatic Display Device Using Monochromatic Diffusers, a Beamsplitter and a Combiner in an Optical Processor Space", Ser. No. 60/282,736, filed on Apr. 10, 2001 entitled "Method and Apparatus for Combining Multiple Monochromatic Images Using an Optical Processor Space", Ser. No. 60/282,735, filed on Apr. 10, 2001 entitled "Monochromatic Display Device Using a Monochromatic Diffuser and a Beamsplitter and a Combiner in an Optical Processor Space", Ser. No. 60/282,737, filed on Apr. 10, 2001 entitled "Polychromatic Display Device Using a Chromatic Combiner, and Achromatic Diffuser and a Beamsplitter and a Combiner in an Optical Processor Space", Ser. No. 60/282,734, filed Apr. 10, 2001 entitled "Polychromatic Display Using Monochromatic Diffusers, a Beamsplitter and a Combiner in an Optical Processor Space".

FIELD OF THE INVENTION

The invention relates to projection displays and more particularly an improved method of homogenizing and formatting the light from a light source to produce higher uniformity and efficiency in the projected image.

DESCRIPTION OF RELATED ART

Illumination systems used for image projectors are designed to generate a spatially uniform plane which can be used to illuminate an imaging device, film or other media. The reflected or transmitted light from the imaging device is then projected onto a screen for viewing. The brightness and spatial brightness uniformity should be within certain limits for each particular application to be considered acceptable to the viewers.

Image projectors including film movie projectors, slide projectors, electronic liquid crystal and micro-electro-mechanical (mem) projectors, microfilm and overhead projectors all require a high degree of spatial light uniformity in the image to produce a pleasing image. This has always been a challenge for projection system designs due to the fact that the light sources available for these systems all have very disorganized light output and therefore require complex optical systems to organize the light. Additionally, high degrees of magnification in short distances (which often occur in these optical systems) cause a problem which is well known in the optical field—the $\cosine^4$ roll off of power in the image as you move radially away from the center of the image. This effect is most predominant at the corners of the image. Another problem is that light sources tend to produce round or elliptical gaussian beam profiles, while most images are rectangular in format. Typically, the light beam is spatially truncated (i.e., the portions of the beam which fall outside a rectangular profile that corresponds to the image are blocked). This leads to another problem, which is maximizing the brightness of the illumination—when the light is truncated to change its geometry, the truncated light is obviously wasted.

Many optical methods have been used in the prior art to try to minimize the variations in uniformity which are due to the particular characteristics of the available light sources as well as to maximize the brightness of the illumination. The optical method used depends somewhat on the light source used. Many different types of light sources are in common use today. Some types are electric filament, and arc lamps including metal halide arc, low and high pressure mercury arc, xenon arc, carbon arc, as well as solid state Light Emitting Diode (LED) sources, and Lasers. Not all of these light sources, however, are suitable for displays using prior art technologies.

Two of the most common types of light sources in use in commercial applications are metal halide arc lamps and high pressure mercury arc lamps. These arc lamps are usually configured in an optical illumination system which employs an elliptical or parabolic reflector to gather and direct the light to a focal point or collimated beam respectively, as shown in FIG. 1. Both of these types of systems produce highly non-uniform beams. Some systems use reflective tunnels or light pipes through which the source light is channeled in order to create a scrambled, hence more spatially uniform bundle of light rays as shown in FIG. 2.

Lenslet arrays are also sometimes used to increase the uniformity of the light. Some versions of these lenslets are described in U.S. Pat. Nos. 5,098,184 and 5,418,583. The lenslet arrays function essentially in the following manner. Two lenslet arrays are separated by a distance equal to the focal length of the individual elements. The elements of the first array form an image of the source in the aperture of the elements of the second array. In the case of a laser, the source image is a diffraction pattern. The elements of the second array then form an image of the aperture of the elements of the first array on the illumination plane. The aperture is chosen to match the aspect ratio of the device (film gate, or LCD) to be illuminated. A field lens in close proximity to the second array focuses the chief rays of each element to the center of the illumination plane so that the subsets of the beam sampled by all elements of the arrays are superimposed at the illumination plane and an averaging process thus occurs that causes the illumination plane to have more uniform irradiance. A second field lens is often required at the illumination plane to ensure that the light is telecentric as most often required by projection imaging optics.

In this manner a beam with non-uniform irradiance may be sampled by arrays composed of many elements and converted to a uniform beam with a different geometry (generally rectangular).

The lenslet array optical system which is used in an illumination system has design characteristics that must be adjusted to ensure that the illumination and imaging systems are compatible. If they are not, then light is wasted. For example, the geometry of the illumination should be the same as the geometry of the imager. The numerical aperture of the illumination system should also be compatible with the imaging system. The ratio of the footprint of light incident on the first array to the distance to the illumination plane determines the numerical aperture of the illumination light. Thus the focal length of the array elements and the field lens focal lengths are adjusted to ensure that the illumination numerical aperture matches the imaging numerical aperture.

At first blush, laser light appears to have enormous potential for being the illumination source in projection display systems. The light is well behaved and organized (i.e.: it is collimated), it is chromatically pure, and with a minimum of three wavelengths (Red, Green, and Blue) a high color space or gamut can be created, and high power low cost lasers are becoming available. There are, however, several problems with laser-based illumination systems.

First, the coherency of laser light leads to speckle, which is a fine-grained non-uniformity. The speckling effect is increased with the use of so-called holographic diffusers as proposed in this invention. The net effect is often a high frequency mottling effect sometimes called "worminess." Another problem is that the laser light is collimated and, as such, it is difficult to create a cone or numerical aperture which will allow an image to be projected onto a screen, as with a projector. Yet another problem is that the laser light typically has a gaussian intensity profile and it may have a wide range of diameters, depending upon the particular laser source which is used. This can, and often does, lead to a non-uniform light distribution on the final screen or projected image surface.

Another problem is that currently available lasers typically do not have enough power to provide sufficient illumination in some display devices. Further, using prior art methods, it is difficult to combine the beams of multiple lasers to obtain sufficient illumination for this purpose.

Another problem with the use of laser light as a display illumination device is that the beam generated by a laser may be astigmatic in its divergence. In other words, the divergence in the beam's cross section may be greater in one axis than another. This causes additional processing problems compared to a circularly symmetric diffraction limited beam.

Yet another problem with the use of laser light in a display illumination device is that, if laser light is diffracted in an optical system, a certain amount of light passes through the diffracting device without being diffracted. This effect is referred to as zero-order light leak. Zero-order light leak may prevent the resulting diffraction pattern from conforming to a well-defined, desired function.

Another problem with using laser light sources for illumination is that they are monochromatic. Since it is desirable to have a source of white light, it may be necessary to combine laser light beams of several different wavelengths (e.g., red, green and blue.) This may be difficult because many optical systems and components are wavelength-dependent and may therefore require color correction to provide even illumination.

Another problem with the use of laser light in display systems is that a large physical volume is normally required. The space requirements of these systems results in part from the separate processing of the laser illumination light in a first optical system and the subsequent processing of the image information in a second optical system so that it can be displayed for viewing.

Yet another problem with the use of laser light in a display illumination device is that optical processors for formatting the illumination image from the laser source are configured to provide a single fixed illumination aspect ratio format. To obtain a different aspect ratio format for use in the display, the illumination source is typically masked, so a portion of the light is lost and significant system efficiency is lost. In order to utilize all of the light generated by the laser source, it may therefore be necessary to use an entirely different optical processor.

SUMMARY OF THE INVENTION

One or more of the problems outlined above may be solved by the various embodiments of the invention. The present invention performs a similar function as a lenslet array optical system, but does so more effectively, with fewer and lower cost components, and with improved design flexibility. The present techniques may be applied to many types of illumination sources such as arc lamps and LED's in addition to lasers.

Broadly speaking, the invention comprises a system and method for converting a laser beam having a non-uniform profile into a source of illumination which has uniform power density. The generated illumination image may be used for a variety of purposes. For example, the image may be a uniformly intense rectangle suitable for use in a display device, or it may be a round dot suitable for transmitting the light into an optical fiber. The present invention can be used to conserve the power generated by the laser source and direct substantially all of the power into the desired illumination region. Laser speckle artifacts can also be reduced or eliminated at the same time. The choice of design of the elements in the system allows for precise control of the illumination pattern and the particular telecentric cone angle patterns exiting the illumination pattern. While the preferred embodiment uses a laser source, the system is capable of utilizing a wide variety of light source devices, including all arc lamps and LED sources.

The operation of a system in accordance with one embodiment of the invention is as follows. A block diagram of the system is shown in FIG. 4. A beam of light is first generated by the laser light source. The light beam is expanded or sized to illuminate a controlled angle diffuser. The expanded beam remains collimated.

The expanded beam is passed through a controlled angle diffuser (e.g., hologram, bulk scatterer, etc.) to diffract or direct the light in a predetermined pattern. (Crossed lenticular arrays, or lenslet arrays can also be used.) The controlled angle diffuser can be designed to emit light angularly in any geometry (such as rectangular to match a display device aspect ratio). The angular emission of a holographic diffuser is similar to the aperture geometry of the lens array system described above. It should be noted, however, that in the prior art it takes two optical elements with an intervening space to produce an effect which is performed by a single optical element (the holographic diffuser) in the present system.

A first field lens is positioned following the holographic diffuser. This first field lens focuses and spatially overlays the diffracted light onto a single rectangular plane which lies at a distance from the lens equivalent to its focal length. A second field lens is used at this illumination plane to correct for the degree of telecentricity desired in the system. In some cases, over-correction or under-correction may be desired. This image is then used as the illumination source for a display. Both field lenses function identically to field lenses in lens array systems, but at significantly lower cost.

The present systems and methods may provide a number of advantages over prior art. For instance, the level of light efficiency may be substantially increased over the prior art. Further, the problems often encountered in coherent optical systems relating to speckle and image "worminess" (high frequency intensity variation) may be reduced or eliminated. Another advantage is that the illumination provided in this manner is uniform and can be spatially formatted to match the display device being illuminated (rather than providing illumination with the gaussian intensity falloff which is common in prior art designs).

An alternative to the holographic diffuser is a crossed lenticular array as shown in FIG. 5A. The crossed lenticular array performs the same optical function as the hologram for a rectangular emission profile, but at a lower spatial sampling rate. The lens profiles in the lenticular can be aspheric to compensate for uniformity issues as described above. The crossed lenticulars can be combined into one element as shown in FIG. 5B. An additional configuration is to integrate the crossed lenticular function into a single element lenslet array as shown in FIG. 5C. While the lenslet arrays reduce the beam sampling rate and thereby slightly reduce the resulting image uniformity, they are significantly more achromatic than holographic diffusers and can therefore be used with polychromatic light sources. This embodiment also provides a significant advantage over the prior art in that it does not require the intervening space and volume between the prior art lenslet arrays and thereby allows for construction of more compact systems.

BRIEF DESCRIPTION OF THE DRAWINGS

A better understanding of the present invention can be obtained when the following detailed description of the preferred embodiment is considered in conjunction with the following drawings.

DESCRIPTION OF THE PREFERRED EMBODIMENT

A preferred embodiment of the invention is described below. It should be noted that this and any other embodiments described below are exemplary and are intended to be illustrative of the invention rather than limiting.

In broad terms, the present invention comprises a system and method for processing a laser light beam in an optical system that uses a controlled angle diffuser to produce an image of predetermined shape and intensity.

Figure 1:
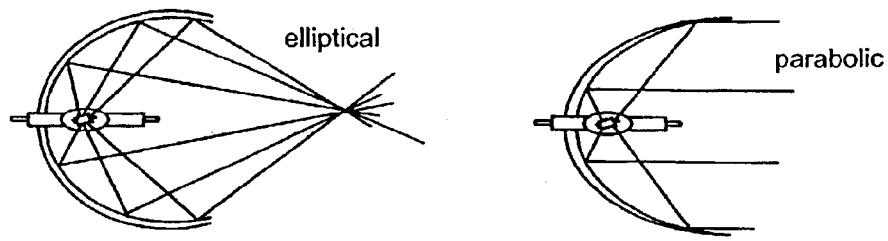
FIG. 1 is a diagram illustrating ellipitical and parabolic arc lamps in the prior art.
Figure 2:
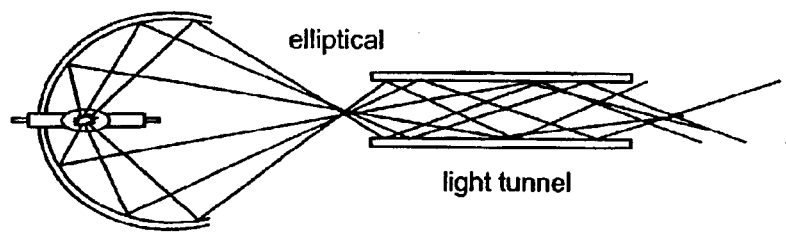
FIG. 2 is a diagram illustrating an elliptical arc lamp and light tunnel homogenizer in the prior art.
Figure 3:
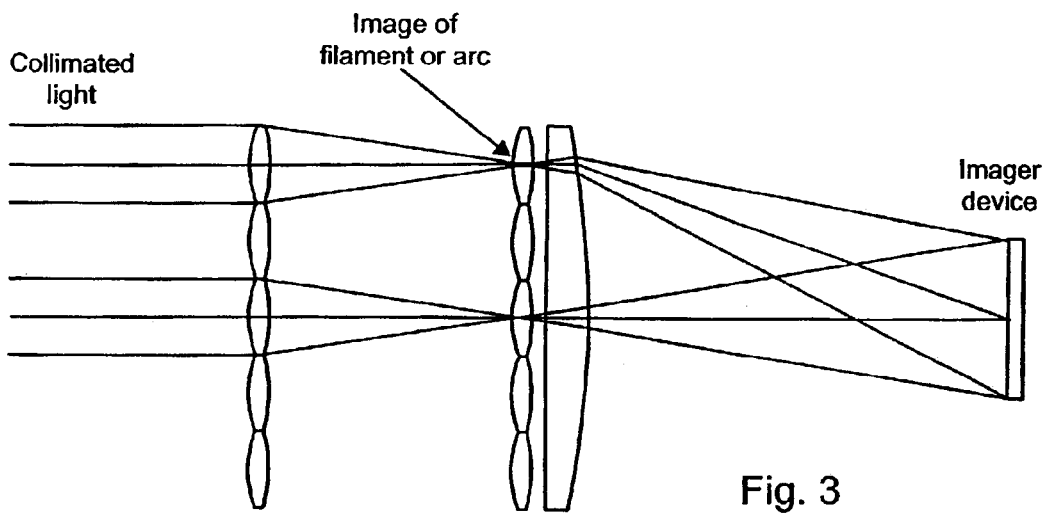
FIG. 3 is a diagram illustrating a lenslet array in the prior art.
Figure 4:
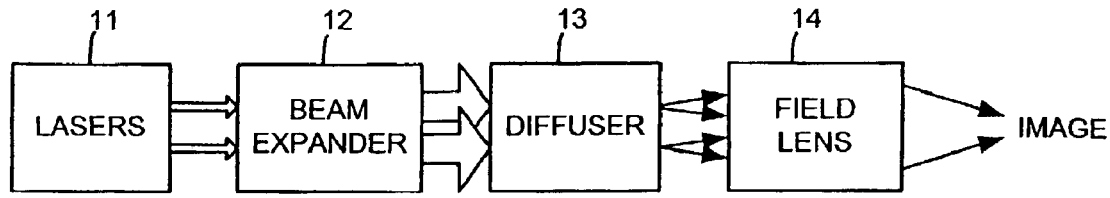
FIG. 4 is a functional block diagram of an illumination system in accordance with one embodiment of the invention.
Figure 6:
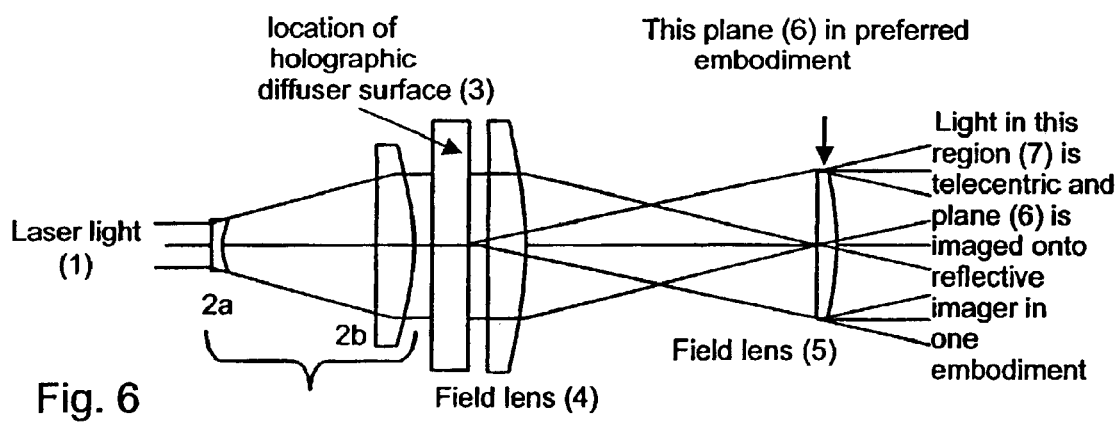
FIG. 6 is a diagram illustrating the components of an illumination system in accordance with one embodiment of the invention.

Referring to FIG. 6, a preferred embodiment of the invention is shown. The invention comprises a laser light source 1, a beam expansion and collimating section 2, a holographic diffuser 3, a first field lens 4, and a second field lens 5. In this embodiment, all elements are coaxially centered. The function of the optical processing by the component elements is to convert the incoming substantially collimated round Gaussian laser beam to a uniform rectangular illumination plane 6 for use in illuminating a spatial light modulator such as a liquid crystal display panel (or any other type of imager). The spatial light modulator can either be illuminated immediately following the field lens 5 or the illumination plane 6 can be optically relayed with or without magnification to another position in the system.

Figure 7:
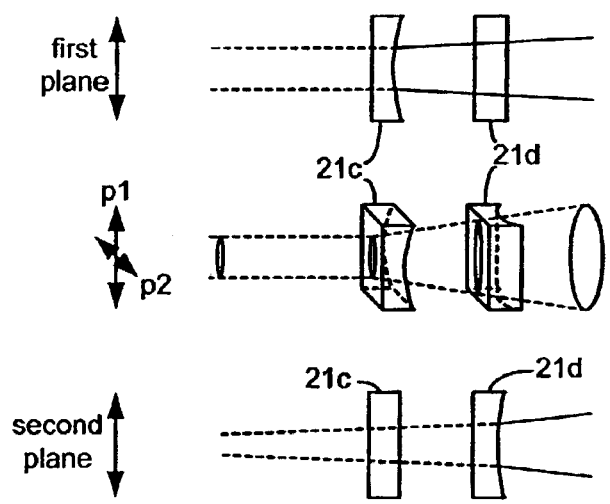
FIG. 7 is a set of diagrams illustrating an optical system designed to expand a light beam from a diode edge emitter laser beam optics by varying degrees in orthogonal planes.

The laser light source in one embodiment may comprise an edge emitting laser. Typically, such a laser emits light in a pattern which has different orthogonal divergences. That is, the emitted beam diverges more in a first plane than in a second plane. The beam must therefore be corrected by an optical system (e.g., beam expander) which has a different prescription in the first plane than in the second. This may be achieved in one embodiment using a pair of crossed cylindrical lenses of different powers as the diverging lens of the beam expander. The configuration of the pair of cylindrical lenses in this embodiment is shown in FIG. 7. Referring to FIG. 7, it can be seen that the first cylindrical diverging lens 2c causes the beam to diverge in a first plane, but not a second. The second cylindrical diverging lens 2d, on the other hand, causes the beam to diverge in the second plane, but not the first. After the beam has passed through both of the cylindrical diverging lenses, the divergence is equal in both planes and can be collimated by a converging lens. The beam exiting the beam expander is therefore collimated in both planes.

It should be noted that the cylindrical lenses described above may be replaced in another embodiment by a single astigmatic lens which performs the same function (refracting the beam by different amounts along different axes.) Likewise, the correction of the different divergences need not be corrected by the diverging lens(es). It might instead be corrected by a pair of cylindrical converging lenses, or by other elements in the optical system. In another embodiment, the divergence of the beam from the laser light source might already have greater divergence than desired in one plane so that one of the cylindrical lenses might be a converging lens while the other is a diverging lens. Many such variations are possible.

Light Emitting Diodes may also be used as light sources in other embodiments. If an LED is used, an optical system which converts the LED output profile to a substantially collimated beam is positioned following the LED. Optical systems to accomplish this are well known in the art.

The preferred embodiment would use a high power VECSEL (Vertical Cavity Surface Emitting Laser) such as those manufactured by Novalux, Inc and termed NECSEL (Novalux Extended Cavity Surface Emitting Laser) due to its substantially cylindrical beam shape and high power capability.

The ability to modify the system to operate with a wide range of sources and source intensity profiles is one of the advantages that may be provided by the present system.

Laser light 1 is shown entering the system of FIG. 6 from the left. The light is monochromatic and collimated with a typical cylindrical beam diameter of 0.3–3 mm, although other diameters and geometries are feasible. Polychromatic sources such as tunable lasers or pre-combined monochromatic sources may also be used. While the intensity profile of the beam in the preferred embodiment is Gaussian, other intensity profiles and laser multi mode profiles will work as well.

Once a substantially collimated light beam is established a beam expander can be used to expand the beam diameter. The amount by which the beam is expanded is determined by the desired F number (as will be described below). The beam expander may be omitted if the collimated source is of sufficient diameter.

A beam expander (2) expands the light beam and re-collimates the light. In a first embodiment, the beam expander is comprised of two elements and an intervening beam expansion space. In this embodiment a first plano-cave lens 2a is used to create a conical beam divergence symmetrically centered along the optical axis. A second plano-convex lens 2b is used to halt the beam expansion and re-collimate the laser beam into a second larger diameter beam having its divergence minimized so that its rays are substantially parallel to the optical axis. This larger diameter beam is then directed onto a holographic diffuser (3).

Figure 8A:
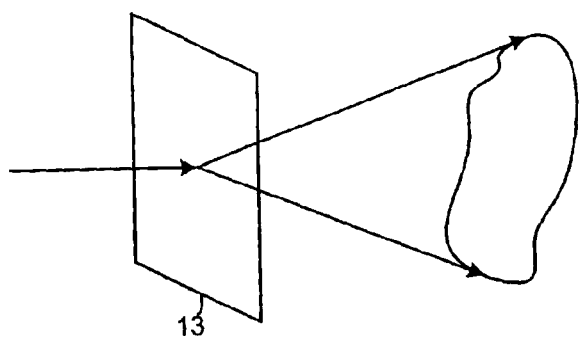
FIG. 8A is a diagram illustrating the profile of a cone of light emerging from a holographic diffuser in one embodiment of the invention.

A holographic diffuser (3) follows the beam expander. In the preferred embodiment this diffuser has the properties of converting an incident laser beam to a plurality of rectangular light cone profiles as shown in FIG. 8C according to the hologram prescription. That is, the light exiting each differential point on the diffuser forms a rectangular cone of light. The rectangular cone of light has its horizontal and vertical orthogonal angles in the ratio of the format of the desired illumination pattern for a display device. In the preferred embodiment, the desired illumination pattern at the output is a uniformly intense rectangle of 4:3 aspect ratio to correspond to standard NTSC television format and standard XGA computer monitor format. In the specific design example shown in FIG. 9, the corresponding angles are $\theta_{Horiz}$=20 degrees and $\theta_{Vert}$=14.8 degrees. The specific horizontal and vertical angles for the 4:3 aspect ratio system or any other format are calculated as follows:

$$\theta_{Horiz} = \text{Arctan}(0.5 \times W_{Image}/D_{diff\text{-}image})$$

$$\theta_{Vert} = \text{Arctan}(0.5 \times H_{Image}/D_{diff\text{-}image})$$

Where: $\theta_{Horiz}$=diffuser horizontal half angle divergence $\theta_{Vert}$=diffuser vertical half angle divergence $W_{Image}$=Half width of the desired Image plane 6

$H_{Image}$=half height of the desired Image plane 6

$D_{diff\text{-}image}$=Distance from diffuser to Image plane 6

Other hologram prescriptions would be used for wide format HDTV, etc.) Each of these light cones is generated from energy from a small section, or sample, of the laser beam Gaussian power profile resulting in a much higher level of uniformity in each light cone than in the original beam. In the preferred embodiment, the center ray of these cone patterns is substantially parallel to the optical axis. Each ray within a given expanding cone has a corresponding parallel ray in all of the other cones being emitted from the surface. All of these parallel rays are at the same angle relative to the central axis. Each set of parallel rays will map to a unique point on the Illumination Plane 6, as a result of the field lens 4 described below. Therefore, the angular pattern of ray divergence defines the shape of the Illumination image at plane 6. Since each point in the Illumination image will be composed of energy from all points in the incoming Gaussian beam, the uniformity of the illumination Plane is substantially improved over the uniformity of the original gaussian beam. The effect is similar to the prior art lenslet array systems whereby each rectangular cone of light is created by sampling the incoming beam at all points and then overlaying the samples on each other at the illumination plane. The Lenslet arrays sample a much lower spatial frequency and therefore produce a less uniform result.

Figure 8B:
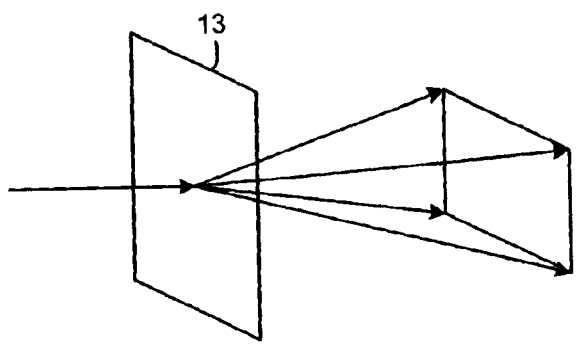
FIG. 8B is a diagram illustrating the profile of a cone of light emerging from a holographic diffuser in an alternative embodiment.
Figure 8C:
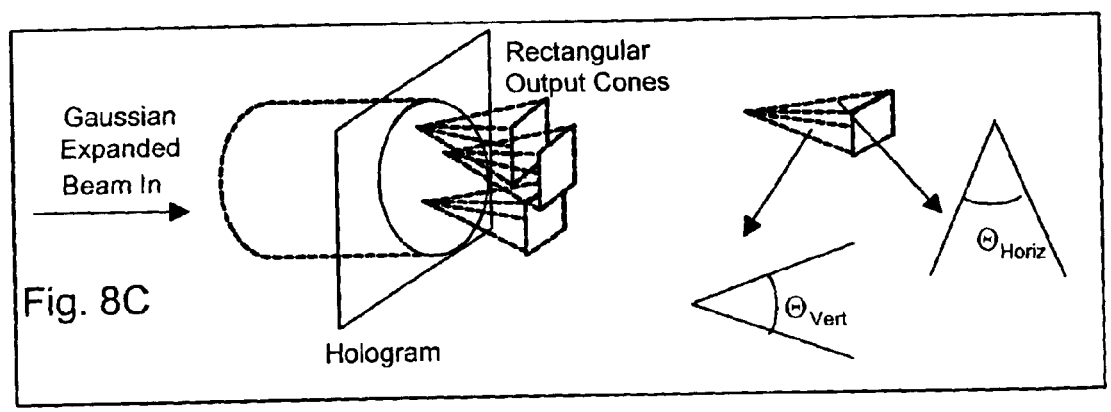
FIG. 8C is a diagram illustrating the profiles of several cones of light emerging from a holographic diffuser in one embodiment.

Other light cone profiles (e.g., circular) are also feasible as shown in FIG. 8B. In fact, the profile may be arbitrarily defined for the application.

The final uniformity is then dependent primarily on the angular power profile of the diffraction pattern of the holographic diffuser. In the preferred embodiment, this profile is that of substantially linear power per degree of solid angle to effect a near uniform power and intensity in the Illumination image. Nonlinear hologram power profiles versus angle of divergence of the light cones can be designed into the hologram to compensate for geometric uniformity problems in the illumination pattern such as the cosine$^4$ power rolloff or other system non-uniformities.

Referring to FIG. 8A, a diagram illustrating the diffraction of light at a single point on a holographic diffuser is shown. As the collimated light passes through the holographic diffuser, it is diffracted so that it exits in a certain cone of light. ("Cone" refers to the solid angle into which the light is radiated.) The cone may be irregularly shaped, as indicated by the dashed line at the right side of the figure if other illumination plane formats are desired. This dashed line is the outline of the diffraction pattern image. The diffraction pattern image is characteristic of the holographic diffuser, and the light emanating from each point on the holographic diffuser radiates outward in a cone of the same shape (i.e., the shape of the image.)

The holographic diffuser can be configured to create any desired diffraction pattern (and corresponding image.) Referring to FIG. 8B, a holographic diffuser configured to generate a rectangular image from each incident point is illustrated. It is contemplated that a holographic diffuser which is configured to generate this type of image will be useful in applications such as projection-type displays, where a rectangular light source is desired. More particularly, the holographic diffusers which are used in display devices can be configured to produce an image which is uniformly intense across its entire area, thereby resulting in a higher-quality image on the display.

It should be noted that the dashed image outlines illustrated in FIGS. 8A and 8B are not themselves images. They are instead representative of the cross-section of the cone into which light radiates from a particular point on the holographic diffuser. Thus, light radiating from a different point on the holographic diffuser will radiate into an identical cone which is displaced laterally from the illustrated cone. While the cones originating at each point on the holographic diffuser are displaced from each other, the image which is produced by passing this light through a field lens and thereby focusing it does not move with the addition of light emanating from new points on the holographic diffuser. Instead, this additional light increases the intensity of the image which has already been formed. The additional light may, however alter the angular extent of the image formed by the lens.

FIG. 8C shows some of the plurality of rectangular patterns generated across the hologram from the area illuminated by the laser beam.

The profile of the illumination footprint on the diffuser controls the angular extent of the light cones exiting the Illumination Plane (6) and thus the numerical aperture or F number of the system. Parallel rays from the diffuser pattern all map to a unique point on the Illumination Plane. The exit angle of that ray from the Illumination Plane 6 is determined by the radial offset of that ray from the image point. The collection of rays which pass through the image point thereby set the light cone shape and divergence corresponding to that point.

Therefore, the diffuser (3) solid cone angle shape (i.e., the diffraction pattern) defines the spatial extent of the Illumination image and the Laser Illumination footprint on the diffuser (3) defines the shape of the light cones and the F number at the Illumination Plane (6.)

Figure 5A:
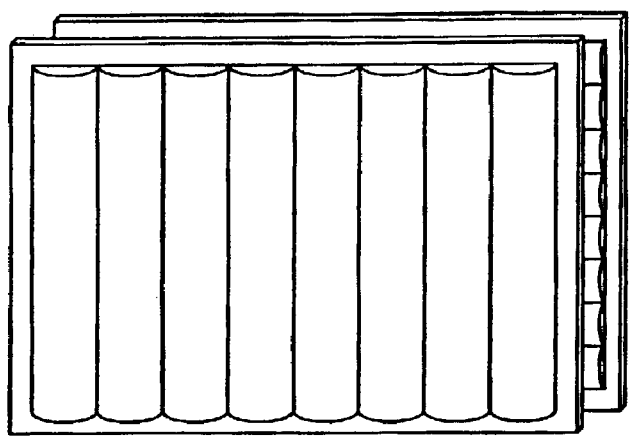
FIG. 5A is a diagram illustrating a lenticular array.
Figure 5B:
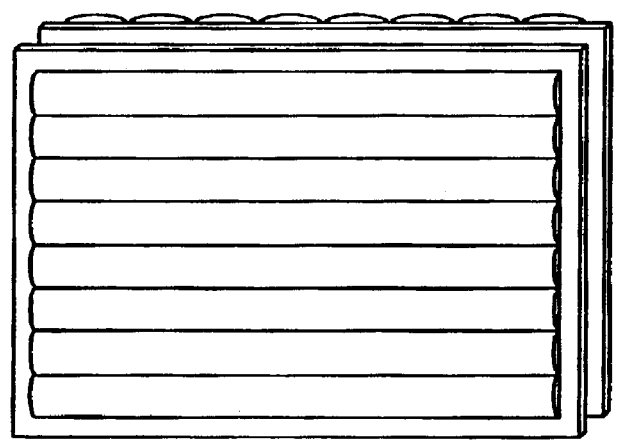
FIG. 5B is a diagram illustrating a compound crossed lenticular.
Figure 5C:
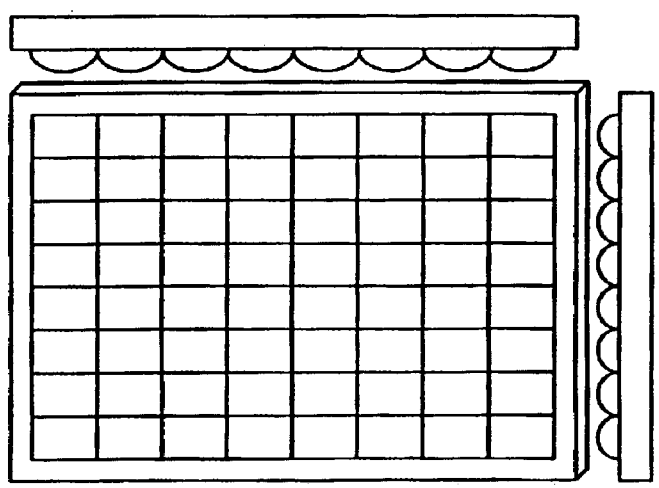
FIG. 5C is a diagram illustrating an integrated crossed lenticular.

In alternative embodiments, crossed lenticular lenses (FIGS. 5A and 5B) or lenslet arrays (FIG. 5C) can be used in place of the holographic diffuser. Both of these alternatives have more achromatic performance and can be used more easily with polychromatic light sources, but they sample the source beam at a lower spatial frequency than a holographic diffuser and may therefore reduce the uniformity of the illumination image relative to the Holographic diffuser embodiment. Aspheric lenslet surfaces may be used to tailor the angular power profile and thereby further improve the Illumination image uniformity.

A first field lens (4) follows the diffuser surface. The field lens 4 maps each parallel ray from the diffuser to a unique point on an Illumination Plane 6 effectively performing and angle to area transformation on the light exiting the diffuser. This process in effect overlays each of the diffuser rectangular cones on each other in the Illumination Plane 6 producing a highly uniform image. The Illumination Plane 6 is located one focal length from field lens (4) and, in the preferred embodiment, produces a rectangular Illumination image having a 4:3 aspect ratio. This should not, however, be considered a limitation, as other values may be viable in a given embodiment, depending on its geometry.

The physical lens may be a common single element lens or it may be a relief fresnel lens or a holographic fresnel lens. An advantage of using any of the fresnel lenses is that they are lower cost and in some cases can be laminated to the diffuser for further assembly simplicity and cost reduction.

A second field lens (5) which has the same focal length as the first field lens is placed at the image plane (6) of the first field lens. The function of this lens is to correct the divergence of the telecentric cone angles exiting the Illumination Plane. Without this lens, the centroid of each light cone bundle exiting the Illumination Plane is directed along a radial from the center of the first field lens (4.) In other words, the centroid of the light cone lies on the line extending from the center of the first field lens to the point at the image plane which defines the vertex of the cone. By adding a second field lens (5) at the Illumination Plane (6) with a focal length equal to the first field lens (4) and having sufficient diameter to circumscribe the entire Illumination Plane image, the light cones exiting the Illumination Plane can be made to have their respective centroid exit angles substantially parallel to the optical axis. This lens can be either overpowered or underpowered, that is its focal length may be adjusted as the imaging optics system requires. This geometry will provide telecentric light in plane (7) which can then be imaged onto a display device such as a reflective or transmissive LCD or similar device.

Figure 9:
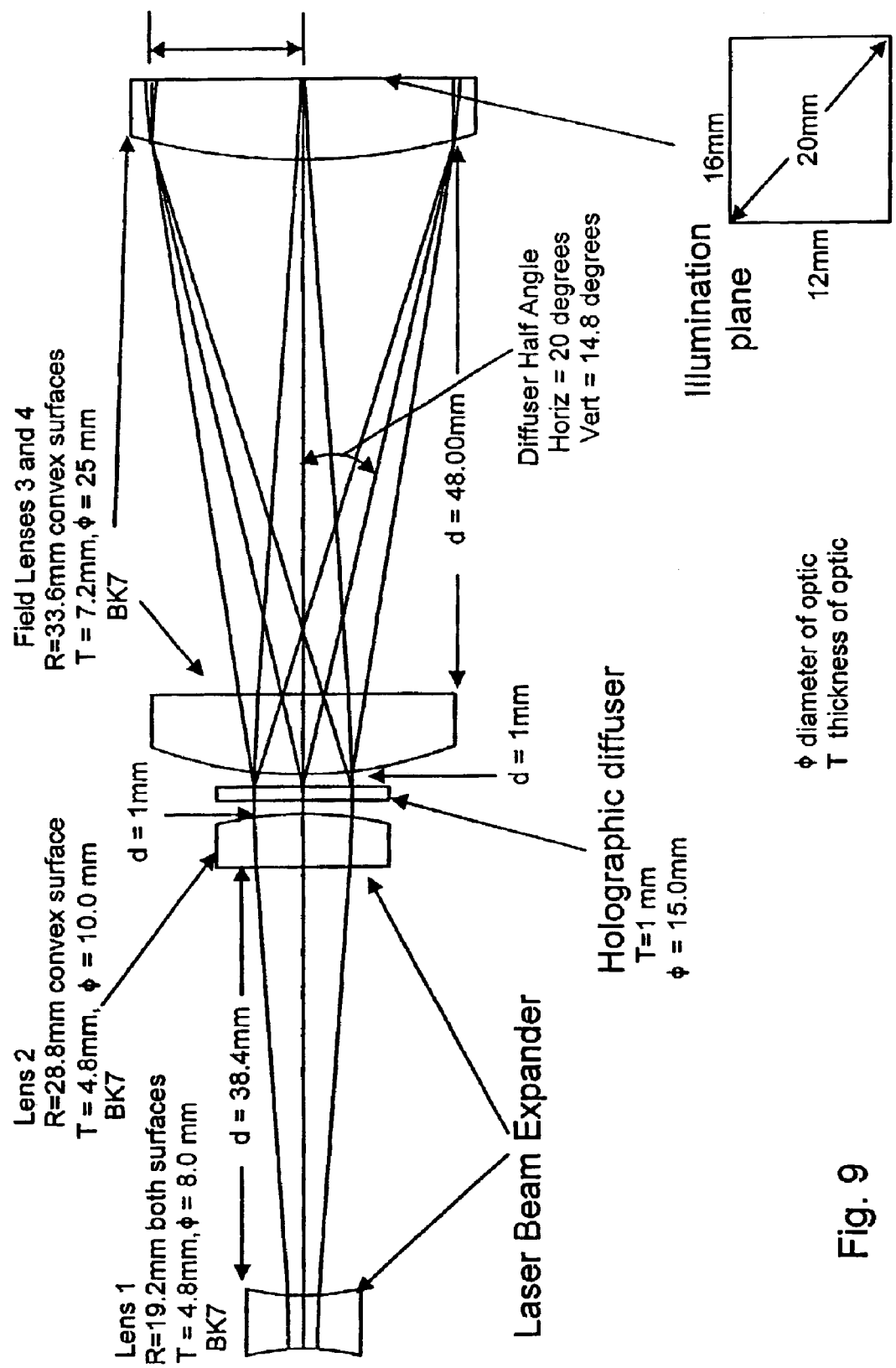
FIG. 9 is a diagram illustrating the specific design of an illumination system in a preferred embodiment.

A specific design example of the preferred embodiment is shown in FIG. 9.

Figure 10:
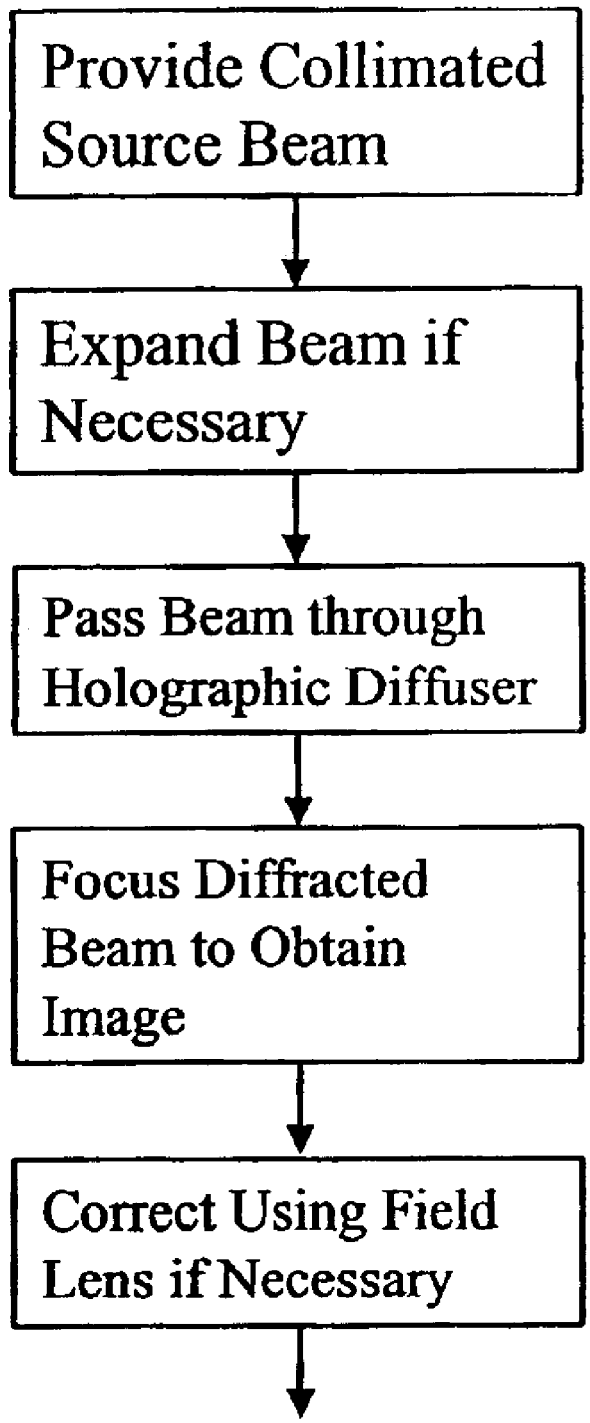
FIG. 10 is a flow diagram illustrating the operation of an illumination system in accordance with one embodiment of the invention.

A functional diagram of the preferred embodiment is shown in FIG. 10.

The optical system described above may be used for a number of purposes. One of these purposes is the illumination of an imager in a projection display device. It is desirable in such devices to have a source of illumination which is uniform and which has a shape corresponding to the shape of the imager used in the device. In this instance, a holographic diffuser which forms such an image can be selected. The optical system can then be configured to focus this image either on a plane which is coincident with the imager of the display device, or on a plane from which it can be transmitted, via relay optics, to the imager.

Several projection system utilizing the invention are shown in FIGS. 11 and 12. These architectures are well known in the art and should be exemplary of how the invention can be used in such systems.

Figure 11A:
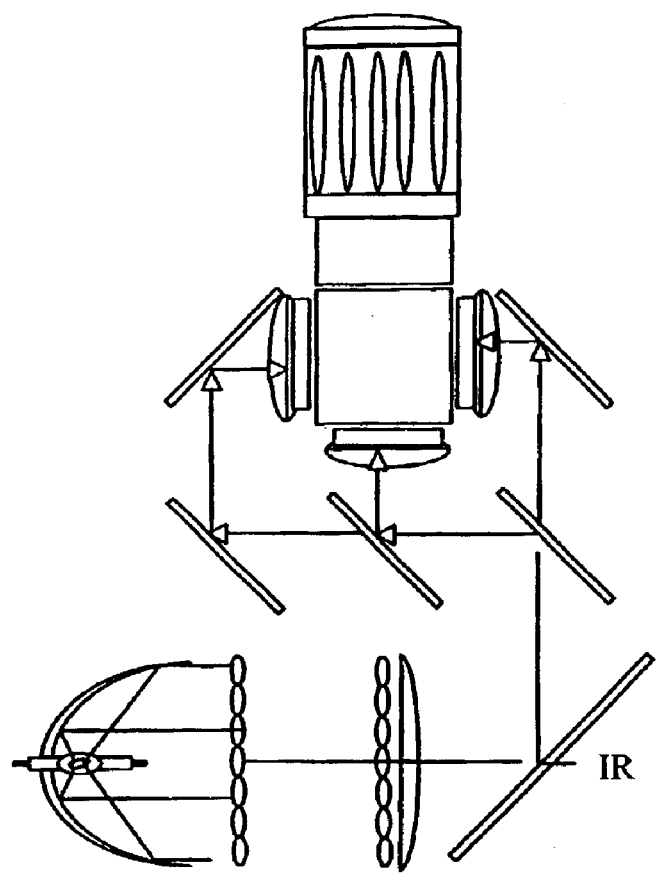
FIG. 11A is a diagram illustrating a prior art transmissive imager system.

FIG. 11A shows a typical prior art system using an arc lamp using three separate imagers for each primary red, green and blue color and three transmissive imagers system for each corresponding primary. In this case optical filters are used to separate the white light from the source into its constituent primary colors.

Figure 11B:
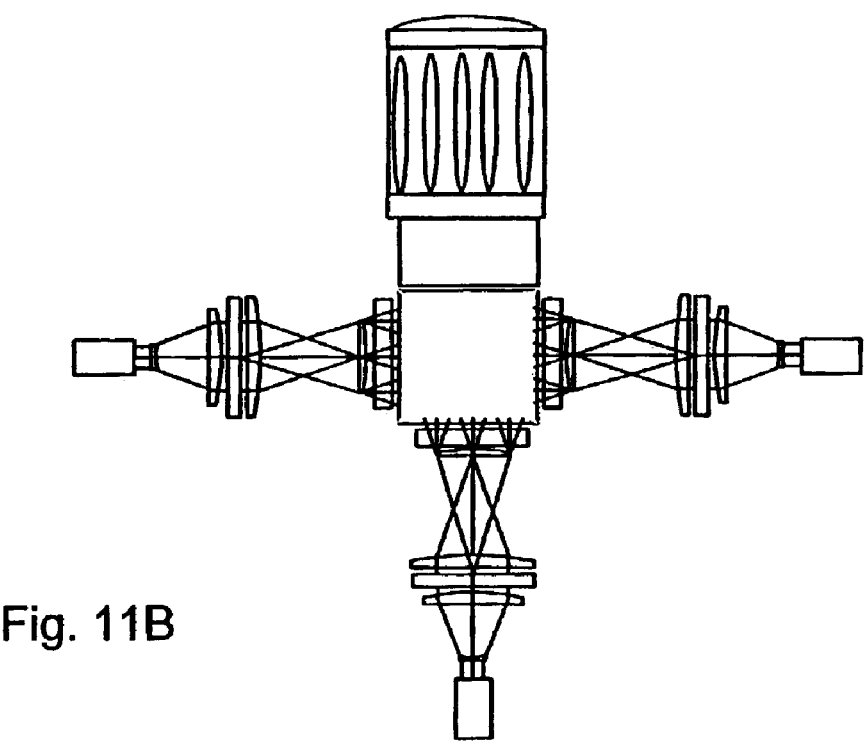
FIG. 11B is a diagram illustrating an embodiment of the present system including a transmissive imager.

FIG. 11B shows a three imager transmissive system which uses three separate imagers for each primary red, green and blue color with three separate monochromatic illumination sources which each comprise the invention. In each of the separate illumination sources, the hologram prescription is designed to operate at a specific monochromatic wavelength so as to produce the same size illumination image to fit the spatial light modulator(the imager) each of which are the same size and shape. In the case of three imager systems, all sources are on continuously.

Figure 12A:
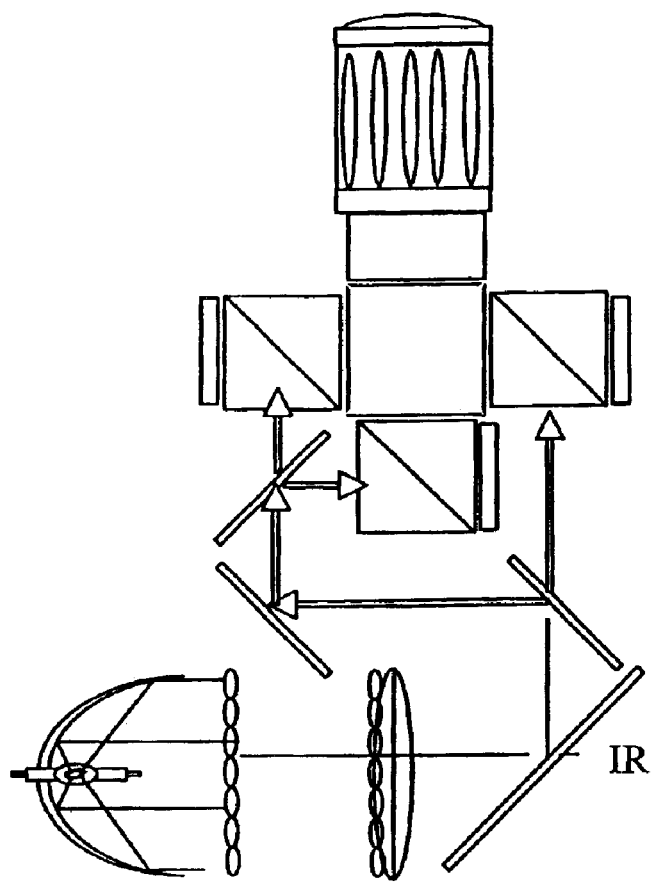
FIG. 12A is a diagram illustrating a Polarizing Beam Splitter/Imager system in the prior art.

FIG. 12A shows a typical prior art three polarizing beam splitter system using an arc lamp using three separate imagers for each primary red, green and blue color and three transmissive imagers system for each corresponding primary. In this case optical filters are used to separate the white light from the source into its constituent primary colors.

Figure 12B:
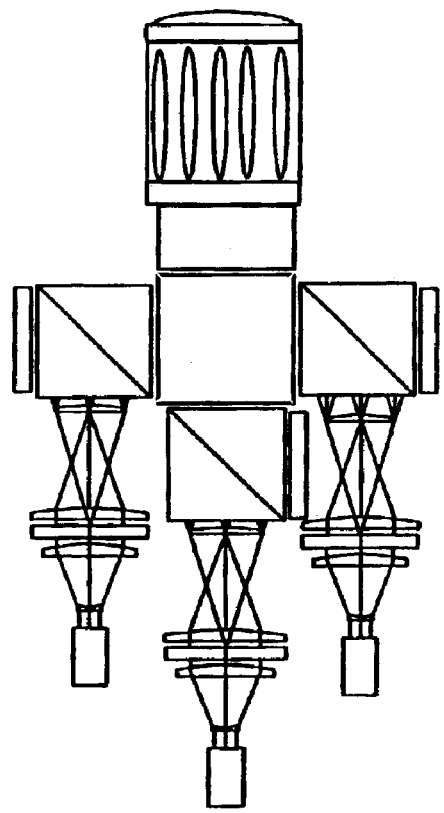
FIG. 12B is a diagram illustrating a Polarizing Beam Splitter/Imager system in accordance with one embodiment of the invention.

FIG. 12B shows a three imager, three beamsplitter reflective imager system using three independent sources comprising the invention as described above.

Figure 13A:
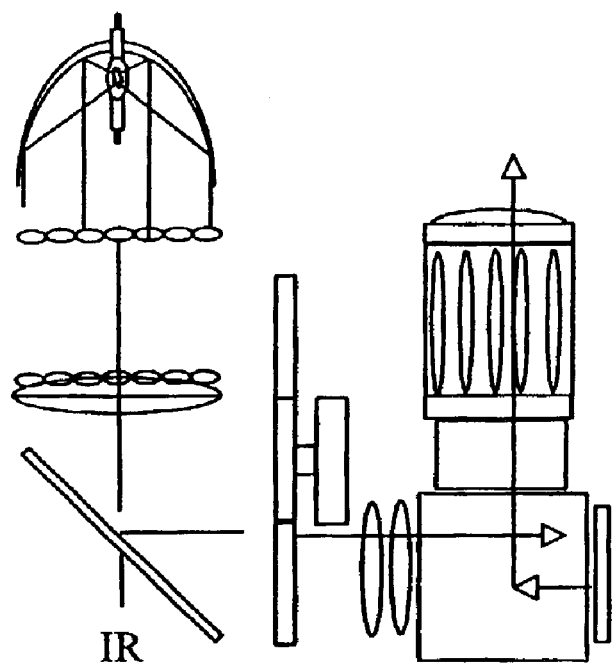
FIG. 13A is a diagram illustrating a Prior art one color sequential imaging system.

FIG. 13A shows a typical prior art one imager color sequential system using an arc lamp source and a color filter wheel for temporal color sequencing. The sources are temporally modulated in sequence with the color information active on the spatial light modulator(the imager.)

Figure 13B:
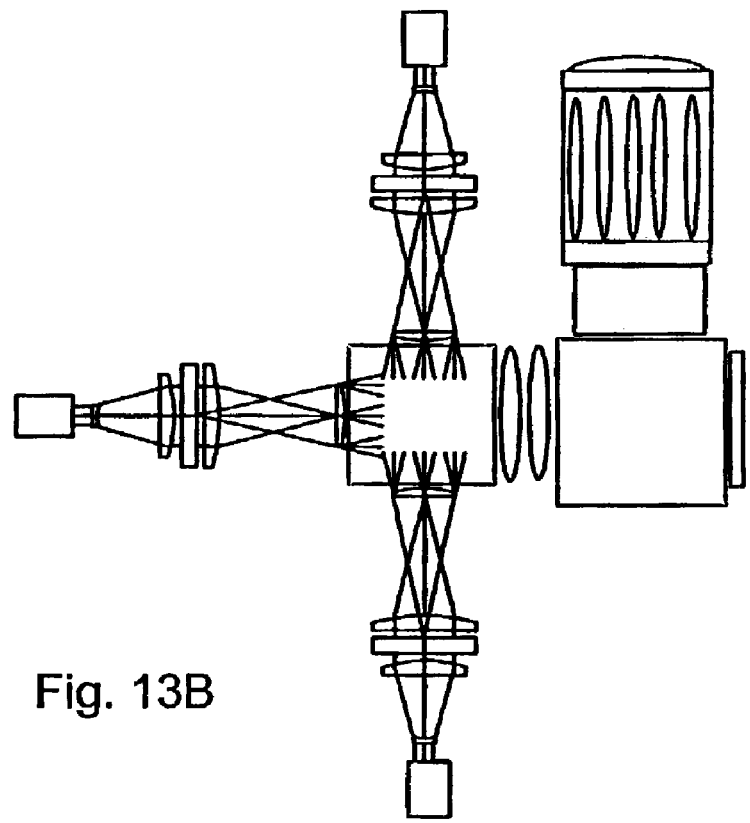
FIG. 13B is a diagram illustrating a color sequential imaging system in accordance with one embodiment of the invention.

FIG. 13B shows a one imager color sequential system also using three independent sources comprising the invention pre-combined by a color combiner to produce a coaxial polychromatic illumination source. The sources are temporally modulated in sequence with the color information active on the spatial light modulator(the imager.)

Another purpose for which the present system can be used is the combination of laser light beams for input to an optical fiber. Laser light sources are currently used in fiber optic communication systems to provide optical signals which are input to the fibers. Often, however, these laser light sources do not provide sufficient power to transmit signals over the desired distances. Using the present system, a plurality of laser light beams can be combined for input to a single fiber. In this instance, a diffuser which images the light beams as a single spot smaller than the diameter of the fiber can be selected. The spot can be imaged onto the end of the fiber, thereby transmitting the light into the fiber. In this embodiment, the aperture of the diffuser and/or corresponding field lens can be selected to ensure that the light which is imaged onto the optical fiber is within the numerical aperture necessary to transmit the light into the fiber.

The benefits and advantages which may be provided by the present invention have been described above with regard to specific embodiments. These benefits and advantages, and any elements or limitations that may cause them to occur or to become more pronounced are not to be construed as a critical, required, or essential features of any or all of the claims. As used herein, the terms "comprises," "comprising," or any other variations thereof, are intended to be interpreted as non-exclusively including the elements or limitations which follow those terms. Accordingly, a process, method, article, or apparatus that comprises a list of elements does not include only those elements but may include other elements not expressly listed or inherent to the claimed process, method, article, or apparatus.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the following claims.

What is claimed is:

1. A system comprising:
    a light source configured to emit highly collimated light rays;
    a controlled angle diffuser configured to receive the highly collimated light rays and to transform each of the light rays into a corresponding light cone having a predetermined profile; and
    a field lens configured to focus the light cones into an illumination pattern.

2. The system of claim 1 further comprising an additional light source configured to emit additional highly collimated light rays, wherein the controlled angle diffuser is configured to receive the additional highly collimated light rays and to transform each of the additional light rays into a corresponding light cone having the predetermined profile, and wherein the field lens is configured to focus the light cones of the additional highly collimated light rays into an additional illumination pattern which is identical to and superimposed on the illumination pattern.

3. The system of claim 1 wherein the light source comprises one of the group consisting of: a laser; a light emitting diode; and an arc lamp.

4. The system of claim 1 further comprising a beam expander positioned between the light source and the controlled angle diffuser, wherein the beam expander is configured to expand the diameter of a collimated light beam formed by the highly collimated light rays and to maintain the collimation of the light beam.

5. The system of claim 4 wherein the beam expander is configured to expand the light beam asymmetrically.

6. The system of claim 1 wherein the controlled angle diffuser comprises a holographic diffuser.

7. The system of claim 6 wherein the holographic diffuser has a prescription which corresponds to an illumination pattern which is uniformly intense.

8. The system of claim 6 wherein the holographic diffuser has a prescription which corresponds to an illumination pattern which is rectangular.

9. The system of claim 1 wherein substantially all of the light rays emitted by the light source are focused into the illumination pattern.

10. The system of claim 1 further comprising a beam expander positioned between the light source and the controlled angle diffuser and configured to expand the diameter of a light beam formed by the highly collimated light rays, wherein the numerical aperture of light at the illumination pattern is controlled by the diameter of the expanded light beam.

11. The system of claim 1 wherein the controlled angle diffuser has a prescription which corresponds to an illumination pattern which is rectangular and uniformly intense.

12. A method comprising:
    providing highly collimated rays of light;
    transforming each of the rays of light into a light cone having a predetermined profile using a controlled angle diffuser;
    focusing the light cones into an illumination pattern; and
    illuminating a spatial light modulator with the illumination pattern.

13. The method of claim 12 wherein transforming the rays of light using a controlled angle diffuser comprises transforming the rays of light using a holographic diffuser.

14. The method of claim 12 wherein providing the highly collimated rays of light comprises providing a laser light beam.

15. The method of claim 12 wherein focusing the light cones into an illumination pattern and illuminating the spatial light modulator with the illumination pattern comprises focusing the light cones into the illumination pattern at a plane which lies on the spatial light modulator.

16. An illumination system for a display device comprising:
    a laser light source configured to emit a highly collimated light beam;
    a holographic diffuser configured to receive the highly collimated light beam and to generate a light cone from each ray of the highly collimated light beam, wherein each light cone has a predetermined profile; and a field lens configured to focus the light cones into an illumination pattern, wherein the illumination pattern has shape and intensity characteristics which match a spatial light modulator of the display device.

17. The illumination system of claim 16 wherein substantially all of the light beam emitted by the laser light source is focused into the illumination pattern.

18. The illumination system of claim 16 wherein the illumination system is configured to generate an identical illumination sub-pattern from each portion of the light beam and to superimpose the identical illumination sub-patterns to form the illumination pattern.

19. The system of claim 1 further comprising a spatial light modulator, wherein the spatial light modulator is positioned at a plane at which the light cones are focused into the illumination pattern.

* * * * *